US00PP29670P3

(12) United States Plant Patent
Olesen

(10) Patent No.: US PP29,670 P3
(45) Date of Patent: Sep. 18, 2018

(54) MINIATURE ROSE PLANT NAMED 'POULPAR101'

(50) Latin Name: ***Rosa* hybrid**
Varietal Denomination: Poulpar101

(71) Applicant: Mogens Nyegaard Olesen, Fredensborg (DK)

(72) Inventor: Mogens Nyegaard Olesen, Fredensborg (DK)

( * ) Notice: Subject to any disclaimer, the term of this patent is extended or adjusted under 35 U.S.C. 154(b) by 0 days.

(21) Appl. No.: 15/330,288

(22) Filed: Sep. 6, 2016

(65) Prior Publication Data

US 2018/0070499 P1 Mar. 8, 2018

(51) Int. Cl.
*A01H 5/02* (2018.01)

(52) U.S. Cl.
USPC ..... Plt./119
CPC ..... *A01H 5/0222* (2013.01)

(58) Field of Classification Search
USPC ..... Plt./101, 116, 119
See application file for complete search history.

(56) References Cited

PUBLICATIONS

UPOV-PLUTO: Plant Variety Database, Oct. 20, 2017, citation for 'Poulpar101'. 1 page.*
Poulsen Roser AS website. http://www.poulsenroser.com/assortment/rose-collections/parade/intan.aspx. Citation for 'Intan' (Poulpar101). 1 page.*

* cited by examiner

*Primary Examiner* — Susan McCormick Ewoldt
*Assistant Examiner* — Karen M Redden

(57) ABSTRACT

A new garden rose plant of the Miniature class which has abundant, orange flowers and attractive foliage. This new and distinct variety has shown to be uniform and stable in the resulting generations from asexual propagation.

1 Drawing Sheet

Botanical designation: *Rosa* hybrid.
Variety denomination: 'Poulpar101'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpar101', originated as a single seedling from the stated cross.

The new variety may be distinguished from its male pollen parent and female seed parent primarily by the following characteristics. The male pollen parent plant has near white flowers, while the new variety has orange flowers. The female seed parent plant has red flowers, while the new variety has orange flowers.

The objective of the hybridization of this rose variety was to create a new and distinct variety for garden use with unique qualities, such as:

1. Uniform and abundant orange flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpar101' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpar101' was selected in the spring of 2012 by the inventor as a single plant from the progeny of the aforementioned hybridization.

Asexual reproduction of 'Poulpar101' by traditional budding and rooted cuttings was first done by Mogens N. Olesen in the nursery in Fredensborg, Denmark in July, 2012. This initial and other subsequent asexual propagations conducted in controlled environments have demonstrated that the characteristics of 'Poulpar101' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar101'.

Specifically illustrated in the drawing are open flowers viewed from the side and above, sepals detached showing receptacle and reproductive flower parts, leaves, flower petals detached, and a flowering branch showing un-opened flower buds. Plants shown are 2 years of age.

DETAILED DESCRIPTION OF THE VARIETY

The following is a description of 'Poulpar101',as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpar071', U.S. Plant Pat. No. 24,549 are compared to 'Poulpar101' in Chart 1.

CHART 1

| | 'Poulpar101' | 'Poulpar071' |
|---|---|---|
| Petal Count | 35 | 70 |
| Flower Diameter | 55 to 60 mm | 50 to 60 mm |
| General Tonality of Flower Color | Blend of Orange Group 24C & Red Group 41C | Orange Red Group 32B |

Flower and Flower Bud

Blooming habit: Continuous.

Flower bud:

*Size.*—Upon opening, 18 mm in length from base of receptacle to end of bud. Bud diameter is 13 mm.

*Bud form.*—Ovoid.

*Bud color.*—As sepals divide petals are Red Group 41A with intonations of Red Group 41C.

*Sepal inner surface.*—Color: Yellow-Green Group 146D. Surface: Lightly pubescent.

*Sepal outer surface.*—Color: Yellow-Green Group 144A with intonations of Greyed-Red Group 181A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—About 25 mm long, 10 mm wide.

*Receptacle.*—Texture: Smooth. Size: 8 mm in height, 10 mm wide. Color: Yellow-Green Group 144A. Shape: Campanulate.

*Pedicel.*—Surface: Smooth. Length: 25 mm. Diameter: mm on average. Color: Yellow-Green Group 144A with intonations of Greyed-Red Group 180A. Strength: Strong.

Flower bud development: Flower buds are borne in clusters of 3 to 5 flower buds per stem.

Flower bloom:

*Fragrance.*—None.

*Duration.*—The blooms have a duration on the plant of approximately 7 to 10 days. Petals fall cleanly away from plant after flowers have fully matured.

*Size.*—Flower diameter is about 55 to 60 mm when open. Flower depth is 28 mm.

*Flower shape.*—High centered, semi double, with a high pointed center which is tightly closed.

Petalage: Under normal conditions, flowers have about 35 petals.

General tonality of flower: Open flowers are a blend of Orange Group 24C and Red Group 41C.

Petal color:

*Upon opening, outer petals.*—Upper surface: Orange Group 27B with intonations of Yellow Group 13C towards basal zone. Towards apex there are intonations of Red Group 38A. Lower surface: Red Group 49A with intonations of Red Group 51A and Red Group 37A.

*Upon opening, inner petals.*—Upper surface: Yellow-Orange Group 19A splashed with Orange-Red Group 35A. Lower surface: Red Group 43C splashed with Yellow-Orange Group 18A.

*Basal petal spots, upon opening.*—Upper surface: Yellow Group 13C. Lower surface: Yellow Group 13C.

*After opening, outer petals.*—Upper surface: Orange Group 27B with intonations of Yellow Group 13C towards basal zone. Towards apex there are intonations of Red Group 38A. Lower surface: Red Group 49A with intonations of Red Group 51A and Red Group 37A.

*After opening, inner petals.*—Upper surface: Yellow-Orange Group 19A splashed with Orange-Red Group 35A. Lower surface: Red Group 43C splashed with Yellow-Orange Group 18A.

*Basal petal spots, after opening.*—Upper surface: Yellow Group 13C. Lower surface: Yellow Group 13C.

Petals:

*Petal reflex.*—Somewhat reflexed.

*Margin.*—Entire and uniform. No undulations.

*Shape.*—Generally elliptic sometimes broad elliptic. Apex shape: Rounded. Base shape: Rounded.

*Size.*—28 mm (l)×25 mm (w).

*Texture.*—Smooth.

*Thickness.*—Average.

Petaloids:

*Size.*—13 mm (l) by 9 mm (w).

*Quantity.*—About 5.

*Shape.*—Elliptic, with a rounded apex and acute base.

*Color.*—Upper surface is Yellow-Orange Group 19A splashed with Orange-Red Group 35A. Lower surface is Red Group 43C splashed with Yellow-Orange Group 18A. There is a petal spot of Yellow Group 13C on upper and lower surfaces.

Reproductive flower parts:

*Pollen.*—None observed.

*Anthers.*—Size: 2 mm in length. Color: Yellow-Orange Group 17C. Quantity: 30 on average.

*Filaments.*—Color: Greyed-Yellow Group 1C. Length: 3 mm.

*Pistils.*—Length: 4 to 5 mm. Quantity: 20 on average.

*Stigmas.*—Color: Green-White Group 157A.

*Styles.*—Color: Green-White Group 157A.

*Location of stigmas.*—Superior in location relative to the length of the filaments and the height of the anthers.

*Hips.*—None Observed.

Plant

Plant growth: Upright, bushy. Plants are about 32 cm in height, and 30 cm wide.

Stems:

*Color.*—Juvenile growth: Yellow-Green Group 144B. Mature growth: Yellow-Green Group 144A.

*Length.*—On average, canes are 12 cm from the base of the plant to the flowering portion.

*Diameter.*—5 mm.

*Internodes.*—On mature canes about 30 mm between nodes.

*Surface texture.*—Young wood: Smooth. Older wood: Smooth.

Long prickles: None observed.

Plant foliage:

*Compound leaf.*—About 80 mm (l)×50 (w).

*Quantity.*—2 or 3 leaves per 10 cm of stem.

*Leaf bearing angle to the stem.*—45 degrees.

*Color of juvenile foliage*.—Upper side: Yellow-Green Group 144A with marginal intonations of Greyed-Purple Group 183A. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: 15 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 17 mm. Diameter: 2 mm.

*Upper surface*.—Color: Yellow-Green Group 144A.

*Lower surface*.—Color: Yellow-Green Group 144A.

*Rachis*.—Length: 30 mm.

*Upper surface*.—Color: Yellow-Green Group 144A.

*Lower surface*.—Color: Yellow-Green Group 144A.

*Leaflet*.—Quantity: Normally 5 leaflets. Margins: Serrated. Size: On average terminal leaflets are 30 mm long, 21 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa,* downy mildew *Peronospora sparsa,* rust *Phragmidium* spp., black spot *Diplocarpon rosae,* and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the Miniature rose class named 'Poulpar101', substantially as illustrated and described herein, due to its abundant orange flowers, disease resistance, and extended period of bloom.

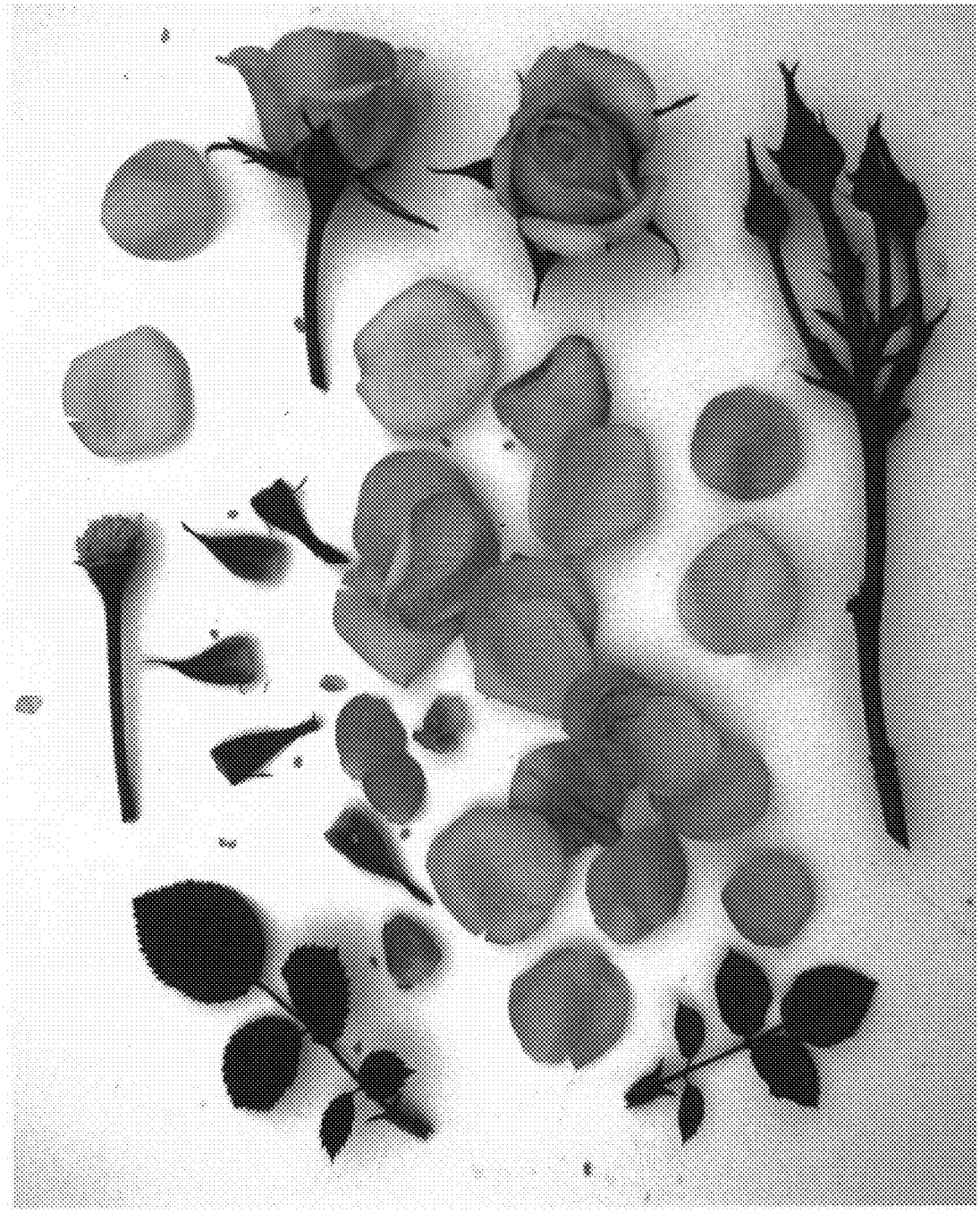

* * * * *